United States Patent
Bar-Tal

(10) Patent No.: US 9,113,824 B2
(45) Date of Patent: Aug. 25, 2015

(54) COMPENSATION FOR RESPIRATORY MOTION

(75) Inventor: Meir Bar-Tal, Haifa (IL)

(73) Assignee: Biosense Webster (Israel), Ltd., Yokneam (IL)

( * ) Notice: Subject to any disclaimer, the term of this patent is extended or adjusted under 35 U.S.C. 154(b) by 442 days.

(21) Appl. No.: 13/017,469

(22) Filed: Jan. 31, 2011

(65) Prior Publication Data
US 2012/0197111 A1    Aug. 2, 2012

(51) Int. Cl.
A61B 5/05     (2006.01)
A61B 5/113    (2006.01)
A61B 5/06     (2006.01)
A61B 5/00     (2006.01)

(52) U.S. Cl.
CPC ............ *A61B 5/113* (2013.01); *A61B 5/063* (2013.01); *A61B 5/721* (2013.01)

(58) Field of Classification Search
USPC ......................................................... 600/424
See application file for complete search history.

(56) References Cited

U.S. PATENT DOCUMENTS

| | | | |
|---|---|---|---|
| 5,391,199 A | 2/1995 | Ben-Haim | |
| 5,730,129 A | 3/1998 | Darrow et al. | |
| 6,298,260 B1 | 10/2001 | Sontag et al. | |
| 6,580,938 B1 | 6/2003 | Acker | |
| 6,597,939 B1 | 7/2003 | Lampotang et al. | |
| 6,711,429 B1 | 3/2004 | Gilboa et al. | |
| 7,263,397 B2 * | 8/2007 | Hauck et al. | 600/374 |
| 7,536,218 B2 | 5/2009 | Govari et al. | |
| 2007/0038078 A1 | 2/2007 | Osadchy | |
| 2008/0221459 A1 | 9/2008 | Craven et al. | |
| 2008/0249424 A1 | 10/2008 | Harlev et al. | |
| 2009/0030307 A1 * | 1/2009 | Govari et al. | 600/424 |
| 2009/0182224 A1 | 7/2009 | Shmarak et al. | |
| 2010/0079158 A1 | 4/2010 | Bar-Tal et al. | |
| 2011/0019625 A1 | 1/2011 | Zhang et al. | |
| 2011/0092809 A1 * | 4/2011 | Nguyen et al. | 600/424 |

FOREIGN PATENT DOCUMENTS

| | | |
|---|---|---|
| CN | 101199416 A | 6/2008 |
| CN | 101657153 A | 2/2010 |

OTHER PUBLICATIONS

U.S. Appl. No. 12/980,488, filed Dec. 29, 2010—Pending.

(Continued)

*Primary Examiner* — Michael Kahelin
*Assistant Examiner* — Mitchell E Alter
(74) *Attorney, Agent, or Firm* — Louis J. Capezzuto

(57) ABSTRACT

A method, including: measuring first positions of a probe fixed at a first point in a body of a patient over at least a portion of a respiration cycle of the patient, and formulating respective indicators of a respiration state of the patient at the first positions. The method further includes generating a functional relationship between the first positions and the respective indicators and extracting parameters from the functional relationship. The method also includes moving the probe to a second point of the body, measuring second positions of the probe at the second point during a subsequent respiration cycle of the patient, and applying the parameters to the second positions so as to compensate for respiratory motion of the patient at the second point.

13 Claims, 4 Drawing Sheets

(56) References Cited

OTHER PUBLICATIONS

Australian Examination Report, Jun. 14, 2014, from co-pending U.S. Appl. No. 12/980,488, filed on Dec. 29, 2010—pending.

Chinese Official Action and Search Report, Sep. 23, 2014, from co-pending U.S. Appl. No. 12/980,488, filed on Dec. 29, 2010—pending.

* cited by examiner

COMPENSATION FOR RESPIRATORY MOTION

FIELD OF THE INVENTION

The present invention relates generally to sensing the position of an object placed within a living body, and specifically to detection and compensation for effects of respiration on the object.

BACKGROUND OF THE INVENTION

A wide range of medical procedures involve placing objects, such as sensors, tubes, catheters, dispensing devices, and implants, within the body. Real-time imaging methods are often used to assist doctors in visualizing the object and its surroundings during these procedures. In most situations, however, real-time three-dimensional imaging is not possible or desirable. Instead, systems for obtaining real-time spatial coordinates of the internal object are often utilized. In these systems compensation for effects of respiration may be required.

U.S. Patent Application 2009/0030307, to Govari et al., whose disclosure is incorporated herein by reference, describes a method for position tracking that includes placing an internal reference probe in a reference location within a heart of a subject, and collecting and processing location coordinates of the probe during one or more respiratory cycles so as to define a range of the location coordinates corresponding to the reference location.

U.S. Pat. No. 6,711,429, to Gilboa et al., whose disclosure is incorporated herein by reference, describes a system and method of displaying at least one point-of-interest of a body during an intra-body medical procedure. The display may be affected by monitoring and displaying the catheter's location throughout a respiratory cycle and also averaging its location over at least one respiratory cycle.

US Patent Application 2009/0182224, to Shmarak et al., whose disclosure is incorporated herein by reference, describes apparatus for generating an organ timing signal relating to an inspected organ within the body of a patient. The disclosure refers to reconstructing a respiratory trajectory.

The description above is presented as a general overview of related art in this field and should not be construed as an admission that any of the information it contains constitutes prior art against the present patent application.

SUMMARY OF THE INVENTION

An embodiment of the present invention provides a method, including:

measuring first positions of a probe fixed at a first point in a body of a patient over at least a portion of a respiration cycle of the patient;

formulating respective indicators of a respiration state of the patient at the first positions;

generating a functional relationship between the first positions and the respective indicators;

extracting parameters from the functional relationship;

moving the probe to a second point of the body;

measuring second positions of the probe at the second point during a subsequent respiration cycle of the patient; and applying the parameters to the second positions so as to compensate for respiratory motion of the patient at the second point.

Typically, extracting the parameters includes computing a centroid of the measured first positions. The method may further include determining respective vectors from the first positions to the centroid. In one embodiment the functional relationship includes a relationship defining the respective vectors in terms of the respective indicators. Compensating for the respiratory motion at the second point may include determining coordinates of the second point in response to the respective indicators and the respective vectors.

In a disclosed embodiment formulating the respective indicators includes affixing electrodes to the body of the patient, measuring impedances between the electrodes while measuring the first positions, and formulating the respiration indicators in response to the impedances. The method may also include measuring further impedances between the probe and the electrodes, and formulating at least one of the first positions and the second positions in response to the further impedances.

In an alternative embodiment, the method includes affixing electrodes to the body of the patient, measuring impedances between the electrodes and the probe, and formulating at least one of the first positions and the second positions in response to the impedances.

In a further alternative embodiment the functional relationship consists of a relation between changes of the first positions and changes of the respective indicators.

There is further provided, according to an embodiment of the present invention, a method, including:

measuring first positions of a probe fixed at a first point in a body of a patient over at least a portion of a respiration cycle of the patient;

formulating respective first indicators of a respiration state of the patient at the first positions;

measuring second positions of the probe fixed at a second point, different from the first point, in the body of the patient over at least a further portion of a further respiration cycle, subsequent to the at least portion of the respiration cycle;

formulating respective second indicators of the respiration state of the patient at the second positions;

generating a functional relationship between the first and second positions and the first and second indicators;

extracting parameters from the functional relationship;

moving the probe to a third point of the body;

measuring third positions of the probe at the third point during a subsequent respiration cycle of the patient; and applying the parameters to the third positions so as to determine coordinates of the third point.

There is further provided, according to an embodiment of the present invention, a computer software product including a non-transitory computer-readable medium having computer program instructions recorded therein, which instructions, when read by a computer, cause the computer to:

measure first positions of a probe fixed at a first point in a body of a patient over at least a portion of a respiration cycle of the patient;

formulate respective indicators of a respiration state of the patient at the first positions;

generate a functional relationship between the first positions and the respective indicators;

extract parameters from the functional relationship;

measure second positions of the probe at a second point of the body during a subsequent respiration cycle of the patient; and apply the parameters to the second positions so as to compensate for respiratory motion of the patient at the second point.

There is further provided, according to an embodiment of the present invention, apparatus, including:
  a probe fixed at a first point in a body of a patient; and
  a processor, configured to:
    measure first positions of the probe over at least a portion of a respiration cycle of the patient,
    formulate respective indicators of a respiration state of the patient at the first positions,
    generate a functional relationship between the first positions and the respective indicators,
    extract parameters from the functional relationship,
    and wherein, after the probe is moved to a second point of the body, the processor is configured to:
      measure second positions of the probe at the second point during a subsequent respiration cycle of the patient; and
      apply the parameters to the second positions so as to compensate for respiratory motion of the patient at the second point.

The present disclosure will be more fully understood from the following detailed description of the embodiments thereof, taken together with the drawings, in which:

DETAILED DESCRIPTION OF EMBODIMENTS

Overview

Embodiments of the present invention provide a system for compensating for respiratory motion applied to a probe in the body of a patient. Electrodes are fixed to the patient's body, and impedances between the electrodes are measured while the patient respires. The impedances change according to a state of respiration of the patient. For example, the impedances for an end-expirium point are different from those when the patient is breathing in. A respiration indicator is generated from the impedances, a value of the indicator corresponding to a state of the respiration.

In a calibration phase of the system, the probe is placed in a fixed position in an organ of the body, such as the heart. While the patient respires positions of the probe in the patient's body are measured, and all movement (such as heart beats) except for that due to respiration is filtered from the positions. The filtered positions are fitted to an orbit in space, and coordinates of a centroid of the orbit are determined.

The values of the respiration indicator (described above) are correlated with respective vectors from the measured orbit positions to the centroid. The correlation may be conveniently performed by expressing coordinates of the orbit positions as a polynomial of the respiration indicator. In this case the respiration indicator acts as a parameter defining the vector to the centroid.

In an operational phase of the system, the probe is moved to a new stationary position in the body's organ. While in this position, and as the patient respires, coordinates of the probe (filtered to remove all but respiration motion) are measured, and respective values of the respiration indicator are also calculated. For each position of the probe the vector corresponding to the respiration indicator (determined in the calibration phase) is added to the probe position, so as to determine the probe position as if respiration motion is not present.

Embodiments of the present invention provide a system for compensating for respiratory motion of the probe on a continuing basis. In addition, and unlike other respiration compensation systems known in the art, the compensation is not gated to a specific point such as the end-expirium point.

System Description

Figure 1A:
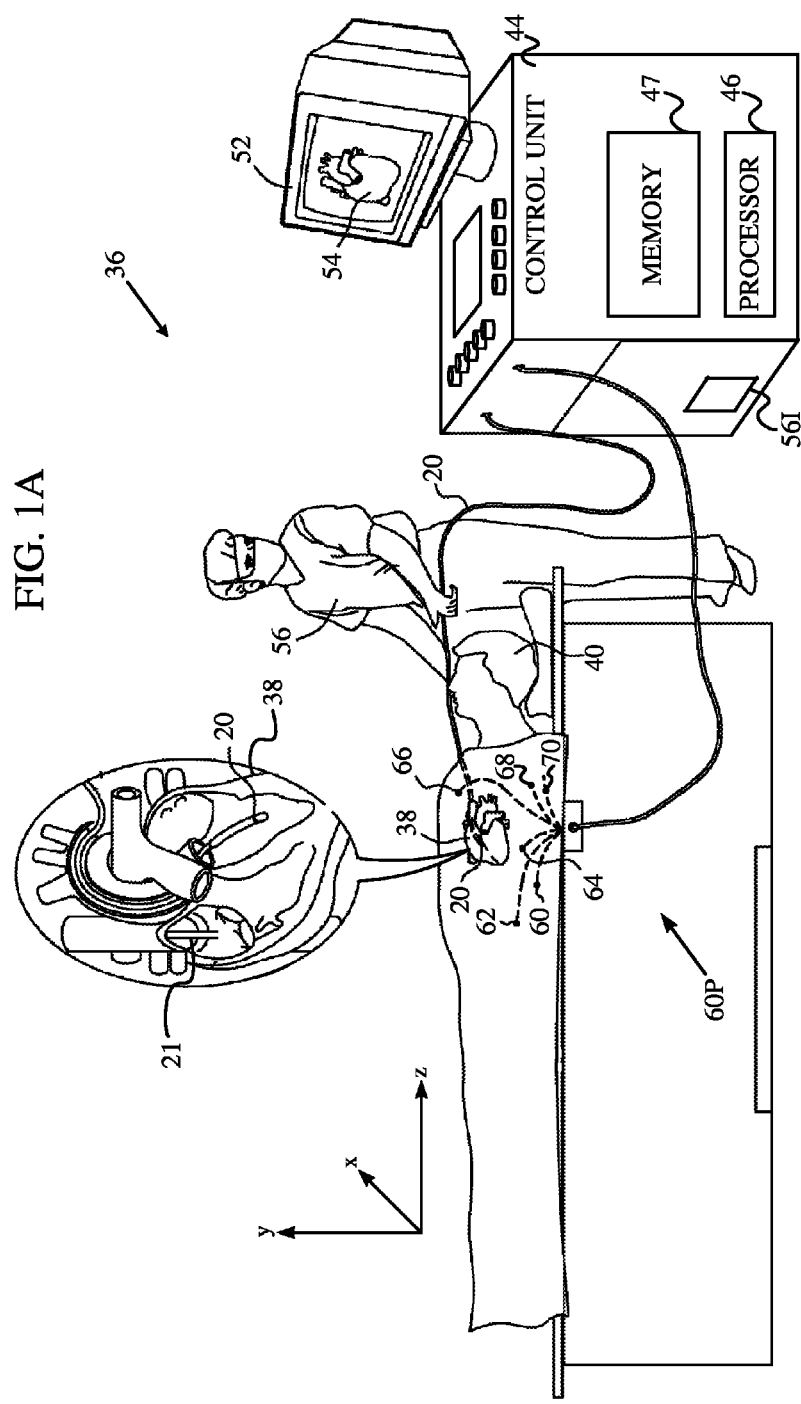
FIG. 1A is a schematic, pictorial illustration of a position sensing system.
Figure 1B:
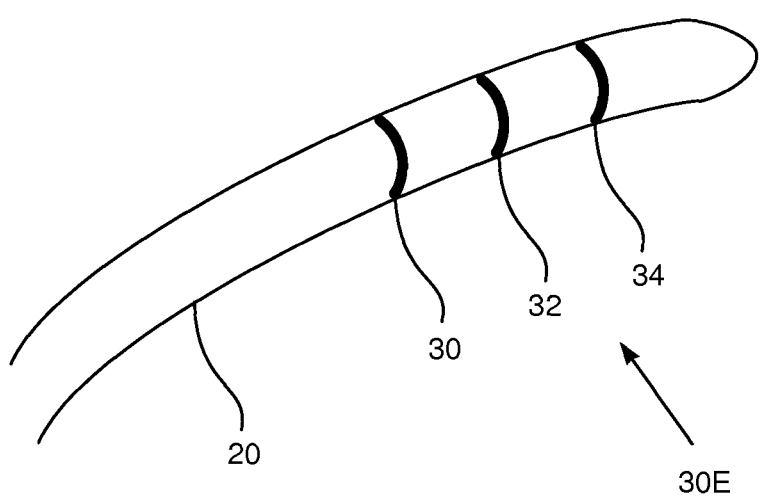
FIG. 1B is a schematic diagram of a probe in the system, according to embodiments of the present invention.

Reference is now made to FIG. 1A, which is a schematic, pictorial illustration of a position sensing system 36 configured to track a catheter probe 20, and to FIG. 1B, which is a schematic diagram of the probe, according to embodiments of the present invention. A medical professional 56 is assumed to operate system 36.

As is described in more detail below, system 36 tracks probe 20 by determining impedances between one or more electrodes on the distal end of the probe, and electrodes on the body of a patient 40, also referred to herein as subject 40. Aspects of tracking systems similar to system 36, which use impedance measurements for tracking, are described in U.S. Patent Application 2010/0079158 to Meir Bar-Tal et al., U.S. patent application Ser. No. 12/980,488 to Meir Bar-Tal, U.S. Pat. No. 7,536,218 to Govari et al., and U.S. Patent Application 2007/0038078 to Osadchy, all of which are incorporated herein by reference.

By way of example, except where otherwise stated in the description hereinbelow, probe 20 is assumed to be used in an invasive procedure within a chamber of a heart 38 of subject 40. Alternatively, position sensing system 36 may be used with probes similar to catheter probe 20 in other body cavities. A control unit 44 is assumed to be used to operate system 36, the unit including a processor 46, typically a computer with appropriate signal processing circuits. The processor uses a memory 47, which typically comprises both volatile and non-volatile data storage devices, wherein data for operating system 36 is stored. The processor is coupled to drive a console 52, which may provide a visual display 54 of the position of catheter probe 20.

As shown in FIG. 1B, probe 20 is assumed herein to have a number of probe-electrodes 30, 32, and 34 that are located at the distal end of probe 20. Probe-electrodes 30, 32, and 34 are also referred to generically herein as probe-electrodes 30E. Control unit 44 comprises alternating current drivers 56I which processor 46 uses to supply currents to the probe-electrodes, and to differentiate between the electrodes the processor sets the alternating frequency of the current supplied to each electrode to be different. The probe-electrodes are connected by wires through the insertion tube of probe 20 to current and voltage measurement circuitry in control unit 44.

In addition, in system 36 there may be other catheter probes comprising one or more electrodes, similar to electrodes 30, 32, and 34. System 36 is able to track these catheter probes, in a substantially similar manner to the method for tracking probe 20. By way of example, one such catheter probe 21 is shown in FIG. 1A. In one embodiment there are approximately 90 frequencies for current drivers 56I, so that up to 90 catheter electrodes may be tracked simultaneously in system 36.

The control unit is connected by wires to body surface electrodes, also referred to herein as body-electrodes, which may be any type of body electrodes known in the art, such as button electrodes, needle electrodes, subcutaneous probes, or patch electrodes. The body-electrodes are typically affixed in galvanic contact with the body surface of subject 40, and receive body surface currents therefrom. Where the following description refers to patch electrodes or patches, it will be understood that embodiments of the present invention may use any of the other type of electrodes described above.

In some embodiments, one or more of the body-electrodes may be positioned in galvanic contact with, and inside, the body of subject 40. Typically, control unit 44 tracks the position of these internally located body-electrodes by any method known in the art. Except where otherwise stated, the following description assumes, for simplicity, that the body-electrodes are located on the body of subject 40. Those having ordinary skill in the art will be able to adapt the description, mutatis mutandis, to cover body-electrodes positioned inside the body of subject 40.

By way of example, body surface electrodes are herein assumed to comprise adhesive skin patches 60, 62, 64, 66, 68 and 70, generically referred to herein as active patches 60P, or by a patch index "i," where i is an integer between 1 and 6. Patches 60P may be placed at any convenient locations on the body surface of subject 40 in the vicinity of the probe. In alternative embodiments of the invention, the body surface electrodes may differ from the exemplary number of 6 electrodes assumed herein. The body surface electrodes receive differing currents from probe-electrodes 30E, and the differing currents are analyzed, typically to evaluate impedances between the body surface electrodes and the probe-electrodes.

The impedances may be used to determine a position and/or an orientation of probe 20 (as is described in the patent and patent applications referenced above). The positions and orientations of probe 20 are assumed to be measured with respect to a reference set of xyz orthogonal axes, illustrated in FIG. 1A, which is typically defined with respect to the position and orientation of subject 40.

Thus, a relation between the position p of the probe and a set of impedances $\{X\}$ is of the form:

$$p = f\{X\} \quad (1)$$

where f is a function of a set of impedances X measured between probe-electrodes 30E and body electrodes 60P. Function f may typically be represented in matrix form.

The function f may be determined experimentally, e.g., as described in the above-referenced U.S. Patent Application 2010/0079158.

Typically, system 36 includes other elements, which are not shown in the figures for the sake of simplicity, and which are referred to as necessary in the following description. For example, system 36 may include an ECG monitor, coupled to receive signals from one or more body surface electrodes, so as to provide an ECG synchronization signal to control unit 44. Typically, system 36 also includes an ablation system operated by control unit 44.

The configuration of FIG. 1A is an example configuration, which is chosen purely for the sake of conceptual clarity. In alternative embodiments, any other suitable configuration can also be used. Typically, processor 46 comprises a general-purpose processor, which is programmed in software to carry out the functions described herein. The software may be downloaded to the processor in electronic form, over a network, for example, or it may, alternatively or additionally, be provided and/or stored on non-transitory tangible media, such as magnetic, optical, or electronic memory.

As described above, patch electrodes 60P are used to find a position for probe 20, by measuring impedances between the patch electrodes and probe-electrodes 30E. Embodiments of the present invention also measure inter-patch impedances, i.e., impedances $m_{ij}$ between patch i and patch j (i, j∈{1, ..., 6}, i≠j). The inter-patch impedances are used to generate a respiration indicator $RI_t$, which is a number representative of a state of respiration of subject 40 at a time t. $RI_t$ may be defined according to equation (2):

$$RI_t = g[m_{ij}] \quad (2)$$

where g is a function, $m_{ij}$ is the impedance between patch i and patch j. As for function f, function g may typically be represented in matrix form.

A method for measuring inter-patch impedances, for determining function g, and thus for evaluating respiration indicator $RI_t$, is described in U.S. Patent Applications 2010/0079158 and Ser. No. 12/980,488 referenced above.

As is described below, processor 46 uses respiration indicator $RI_t$ to compensate for the motion of probe 20 in subject 40, due to the subject's respiration. The motion of probe 20, due to the subject's respiration, is assumed to follow a loop, or an orbit, that is typically repetitive.

Figure 2:
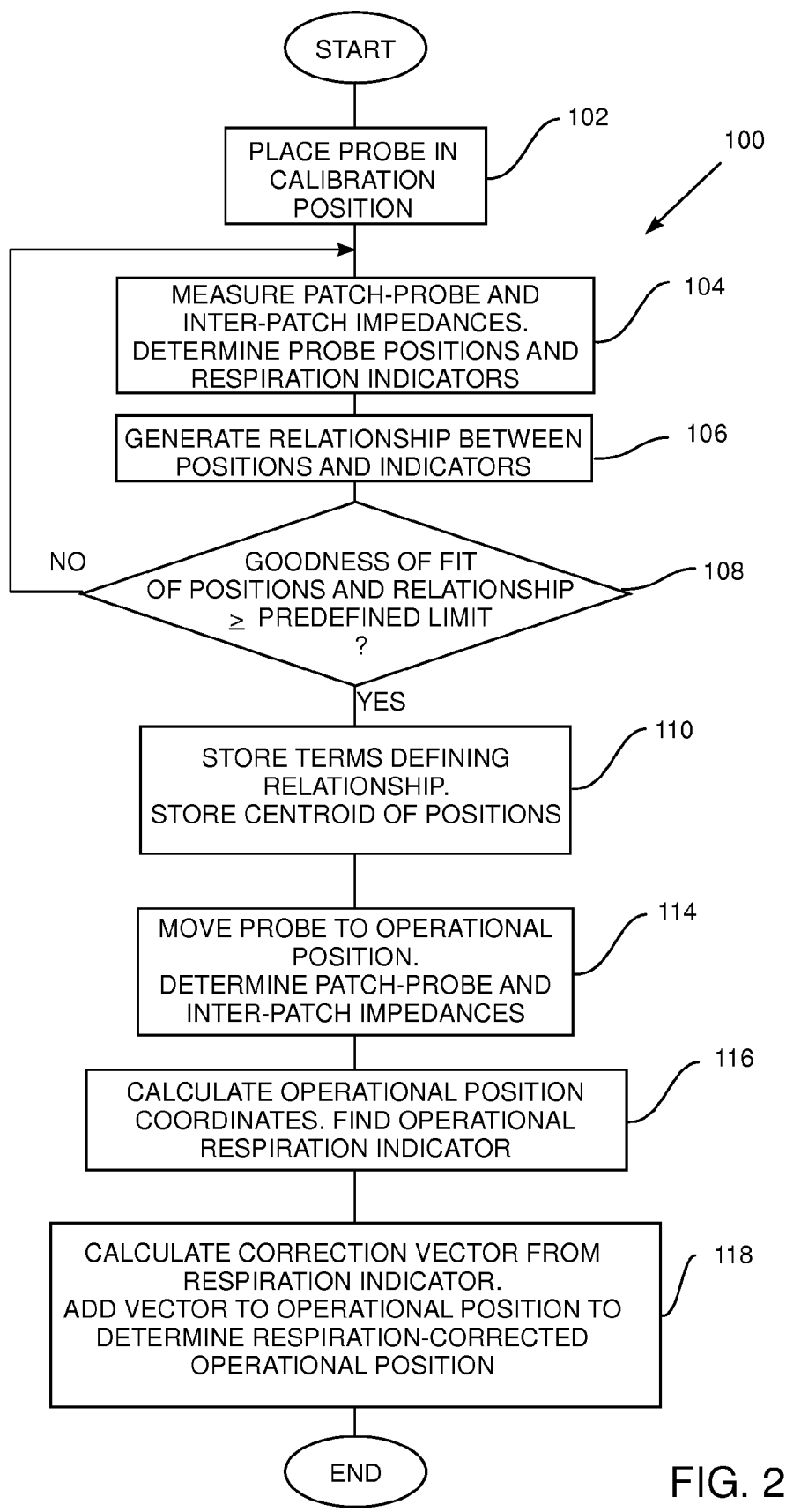
FIG. 2 is a flow chart of a method for compensating for respiration motion of the probe, according to an embodiment of the present invention.

FIG. 2 is a flow chart 100 of a method for compensating for respiration motion of probe 20, according to an embodiment of the present invention. While the description of flow chart 100, for simplicity, is directed to one probe 20 having one probe-electrode 30E, those having ordinary skill in the art will be able to adapt the description, mutatis mutandis, to compensation for respiration motion for other probes, such as probe 21, and/or for probes with multiple electrodes.

The steps of the flow chart are followed by the processor, and assume that processor 46 is able to determine the position of probe 20. By way of example, the processor is assumed to use the impedance measuring method of equation (1) to determine the probe position, but other methods, such as ultrasonic or magnetic location systems may be used instead of, or as well as, an impedance measuring method.

In a first step 102, professional 56 positions probe 20 in a specific point in heart 48, herein assumed by way of example to be the coronary sinus so as allow simple and stable placement of the probe, although any other fixed position may be used. The position of the selected point, herein also referred to as the calibration position, is measured using equation (1) above, so that professional 56 may confirm that the probe is correctly located.

In a calibration measuring step 104, processor 46 records in memory 47, at given instants t in time, a set of patch-probe impedances $X_i$ and a set of inter-patch impedances $m_{ij}$. The recordation is repeated for multiple time instances of a respiration cycle, so that for each time instance there is a set of impedances $X_i$ and a set of impedances $m_{ij}$. Professional 56 ensures that the recordation occurs over at least a portion of a respiration cycle of subject 40, and typically over approximately one to three or more respiration cycles.

From the patch-probe impedances $X_i$ processor 46 calculates respective positions $p_t$ of probe 20, using equation (1), for each of the sets of patch-probe impedances $X_i$. The positions $p_t$ and impedances $m_{ij}$ are filtered to remove non-respiratory motion caused, for example, by beating of heart 48. The filtration typically uses a low pass filter, with a sharp transition between passing and rejected frequencies, so as to preserve only the respiratory frequencies of the signals, while removing frequencies due to the heart beat. (The filtration may be applied during acquisition of the impedance sets, or after the sets have been acquired.) In one embodiment, the filter is a finite element response (FIR) filter which has a 0 dB rejection for frequencies less than 0.2 Hz and a 40 dB or greater rejection for frequencies greater than 0.7 Hz.

From each set of inter-patch impedances $m_{ij}$, the processor also calculates respective values of respiration indicator $RI_t$, using equation (2).

In a model fitting step 106, processor 46 generates a functional relationship between orbit positions $p_t$ and indicators $RI_t$:

$$p_t = P(RI_t) \qquad (3)$$

where P is a function of $RI_t$.

The relationship expressed by function P is typically defined as a polynomial in $RI_t$.

While equation (3) expresses a relationship between positions of probe 20 and respective respiration indicators, it will be understood that an alternative functional relationship may be constructed, using equation (3), relating changes of the positions to changes of the respective indicators.

In a disclosed embodiment the operations of steps 102-106 may be repeated with probe 20 in different stable positions, in each case typically for several respiration cycles. In this disclosed embodiment the different centroids of the orbit (described in more detail below) of the different positions are effectively translated to a common point, and the common point is used in generating the functional relationship of equation (3). The disclosed embodiment effectively averages the results from the different stable positions. For clarity and simplicity, except where otherwise stated, the following description assumes that probe 20 is in one stable position, and those having ordinary skill in the art will be able to adapt the description for embodiments where the probe is in multiple stable positions.

In a condition step 108, the processor performs a goodness of fit analysis between the positions given by equation (3) and the measured position values of the probe determined in step 104. The analysis may be by any convenient method for estimating goodness of fit known in the art. The method is herein, by way of example, assumed to comprise performing a least squares regression analysis between the position values from equation (3) and the measured position values to determine a correlation coefficient.

If the correlation coefficient is less than a preset value, such as 0.9, i.e., if there is a relatively poor fit between the measured position values and the values determined from the respiration indicators using equation (3), the flow chart returns to step 104, so that further positions of the probe are measured.

If the correlation coefficient is at least equal to the preset value, so that there is a relatively good fit between the position values and the values given by equation (3), the processor continues to an orbit-defining step 110.

In orbit-defining step 110, processor 46 stores terms defining the relationship found in step 106 in memory 47. The terms typically include coefficients of $RI_t$, coefficients of powers of $RI_t$, as well as a constant term.

In addition in step 110 the processor calculates and stores a position $(x_c, y_c, z_c)$ of the centroid of the orbit. Processor 46 may compute the position of the centroid of the orbit, typically assuming an equation for the orbit such as equation (3) above, by any method known in the art.

Equation (3) may be conveniently expressed as separate parametric equations (4):

$$x_{RIt} = X(RI_t)$$

$$y_{RIt} = Y(RI_t)$$

$$z_{RIt} = Z(RI_t) \qquad (4)$$

where $(x_{RIt}, y_{RIt}, z_{RIt})$ is a point on the orbit for a specific value of $RI_t$, and $X(RI_t)$, $Y(RI_t)$, and $Z(RI_t)$ are functions of $RI_t$.

The value of $RI_t$ also defines a vector $R_{RIt}$ from point $(x_{RIt}, y_{RIt}, z_{RIt})$ to centroid $(x_c, y_c, z_c)$ according to equation (5):

$$\vec{R}_{RIt} = (x_c - x_{RIt}, y_c - y_{RIt}, z_c - z_{RIt}) \equiv V(RI_t) \qquad (5)$$

where $V(RI_t)$ is a function defining vector $R_{RIt}$.

Step 110 completes a calibration phase of the flow chart.

In a first operational step 114 of an operational phase of the flow chart probe 20 is moved from the calibration position to an operational position in the heart of subject 40. At the operational position, processor 46 records sets of operational patch-probe impedances $X_{io}$ and sets of operational inter-patch impedances $m_{ijo}$. The operational phase of the flow chart assumes that the respiration of subject 40 causes the probe to follow an orbit having generally the same characteristics as that of the orbit followed during the calibration phase.

In a measurement step 116, from each set of operational patch-probe impedances $X_{io}$ the processor calculates a respective operational position $(x_o, y_o, z_o)$ of the probe that has been filtered to remove all motion except for motion due to respiration. The method of determining the operational position, including the filtration, is substantially as described above for calibration measuring step 104.

Also, from each set of operational inter-patch impedances $m_{ijo}$ the processor calculates a respective operational respiration indicator, $RI_o$.

In a vector calculation step 118, the processor calculates a respiration correction vector $R_{RIo}$, using equation (5):

$$\vec{R}_{RIo} = V(RI_o) \qquad (6)$$

The processor adds respiration correction vector $R_{RIo}$ to operational position $(x_o, y_o, z_o)$, to generate coordinates $(x_f, y_f, z_f)$, as in equation (7):

$$(x_f, y_f, z_f) = \vec{R}_{RIo} + (x_o, y_o, z_o) \qquad (7)$$

It will be appreciated that coordinates $(x_f, y_f, z_f)$ are the coordinates of the operational position of the probe, corrected for respiration.

Flow chart 100 then ends.

Figure 3:
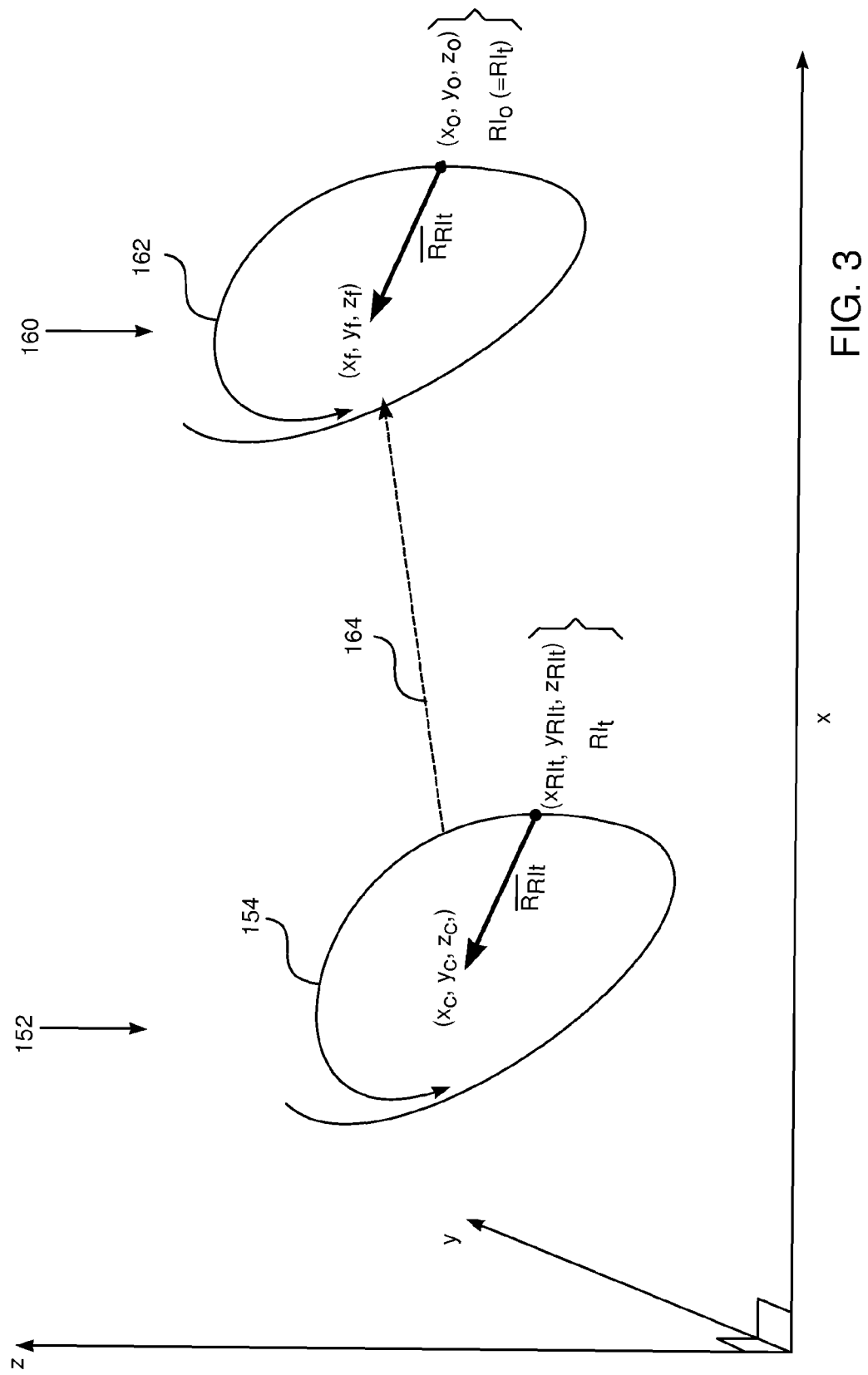
FIG. 3 is a schematic figure illustrating a theoretical motion of a probe, according to an embodiment of the present invention

FIG. 3 (below) and its associated description illustrates the steps of flow chart 100.

FIG. 3 is a schematic figure illustrating a theoretical motion of a catheter probe, according to an embodiment of the present invention. The motion illustrated in the figure exemplifies the motion of probe (or any other probe in heart 38) that is only caused by respiration of subject 40, so that even where there is motion due to beating of the heart, or motion due to other, typically inadvertent, movement of the probe within the heart, such motion is assumed to be cancelled out.

A first diagram 152 schematically illustrates a portion 154 of positions of an orbit. The positions, representing the respiration motion of probe 20, are assumed to be found in the calibration phase of flow chart 100. As described above with reference to step 110, processor 46 calculates a centroid $(x_c, y_c, z_c)$ of the positions of the orbit.

Diagram 152 also illustrates a respiration indicator value $RI_t$ and the associated generic point $(x_{RIt}, y_{RIt}, z_{RIt})$ that are values at time t. Vector $R_{RIt}$, defined by equation (5) is shown in the diagram.

A second diagram 160 schematically illustrates a portion 162 of the respiration motion of probe 20, after the probe has been translated, or moved, to an operational position, as described in step 114 above, i.e., in an operational phase of the flow chart. The translation is schematically illustrated by a broken line 164.

Diagram 160 illustrates steps 116 and 118 of flow chart 100. In step 116 processor 46 determines a value of the respiration indicator $RI_o$, and an operational position $(x_o, y_o, z_o)$ of the probe.

In step 118 the processor determines a respiration correction vector $R_{RI_o}$ using equations (5) and (6). For purposes of illustration correction vector $R_{RI_o}$ is assumed to be identical to vector $R_{RI_t}$ shown for orbit portion 154.

As shown in equation (7), in step 118 the processor adds vector $R_{RI_o}$ to position $(x_o, y_o, z_o)$. The addition provides coordinates $(x_f, y_f, z_f)$, which, as explained above, correspond to the position of probe 20 corrected for respiration.

The embodiments described above assume that correction vectors $R_{RI_o}$ of probe 20 in different positions of an organ such as the heart are generally the same in magnitude and direction. The vectors are determined by the value of respiration indicator $RI_o$.

In an alternative embodiment of the present invention, correction vectors $R_{RI_o}$, derived by applying equation (5) above, may be assumed to vary over the organ. The variation may be measured quantitatively by adapting the operations performed in steps 102-106 of flow chart 100. In contrast to the disclosed embodiment described above wherein in the calibration phase results from the probe in different positions are averaged, in the alternative embodiment the results from the different positions are assumed to generate respective sets of equations (5). There is thus a set of respiration correction vectors for each different position. In the operational phase of flow chart 100, a system of interpolation, typically linear interpolation, may be used to determine an actual correction vector used, based on a measured respiration indicator and the measured position values $(x_o, y_o, z_o)$.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

We claim:

1. A method, comprising:
   measuring first positions of a probe fixed at a first point in a body of a patient over at least a portion of a respiration cycle of the patient;
   formulating respective first indicators of a respiration state of the patient at the first positions, the formulating comprising affixing electrodes to the body of the patient, measuring first impedances between the electrodes while measuring the first positions, and formulating the respective first indicators in response to the impedances;
   measuring second positions of the probe fixed at a second point, different from the first point, in the body of the patient over at least a further portion of a further respiration cycle, subsequent to the at least portion of the respiration cycle;
   formulating respective second indicators of the respiration state of the patient at the second positions by measuring second impedances between the electrodes while measuring the second positions, and formulating the respective second indicators in response to the second impedances;
   generating a functional relationship comprising a relation between changes of the first and second positions and changes of the first and second indicators, respectively;
   extracting parameters from the functional relationship;
   moving the probe to a third point of the body;
   measuring third positions of the probe at the third point during a subsequent respiration cycle of the patient; and
   applying the parameters to the third positions so as to determine coordinates of the third point,
   wherein extracting the parameters comprises computing a centroid of the measured first positions and second positions.

2. The method according to claim 1, and comprising determining respective vectors from the first positions to the centroid.

3. The method according to claim 2, wherein the functional relationship comprises a relationship defining the respective vectors in terms of the respective indicators.

4. The method according to claim 2, wherein compensating for the respiratory motion at the second point comprises determining coordinates of the second point in response to the respective indicators and the respective vectors.

5. The method according to claim 1, and comprising measuring further impedances between the probe and the electrodes, and formulating at least one of the first positions and the second positions in response to the further impedances.

6. The method according to claim 1, and comprising affixing electrodes to the body of the patient, measuring impedances between the electrodes and the probe, and formulating at least one of the first positions and the second positions in response to the impedances.

7. A computer software product comprising a non-transitory computer-readable medium having computer program instructions recorded therein, which instructions, when read by a computer, cause the computer to:
   measure first positions of a probe fixed at a first point in a body of a patient over at least a portion of a respiration cycle of the patient;
   measure first impedances between electrodes affixed to the body of the patient while measuring the first positions,
   formulate first respective indicators of a respiration state of the patient at the first positions, the respective first indicators being formulated in response to the first impedances;
   measure second positions of the probe fixed at a second point, different from the first point, in the body of a patient over at least a further portion of a further respiration cycle of the patient;
   measure second impedances between the electrodes affixed to the body of the patient while measuring the second positions,
   formulate respective second indicators of a respiration state of the patient at the second positions, the respective second indicators being formulated in response to the second impedances;
   generate a functional relationship between changes of the first and second positions and changes of the first and second indicators, respectively;
   extract parameters from the functional relationship;
   measure thirds positions of the probe at a third point of the body during a subsequent respiration cycle of the patient; and
   apply the parameters to the third positions so as to compensate for respiratory motion of the patient,
   wherein extract the parameters comprises computing a centroid of the measured first positions and second positions.

8. Apparatus, comprising:

a probe fixed at a first point in a body of a patient; and a processor, configured to:

measure first positions of the probe over at least a portion of a respiration cycle of the patient, measure first impedances between electrodes affixed to the body of the patient while measuring the first positions, formulate first respective indicators of a respiration state of the patient at the first positions, the respective first indicators being formulated in response to the first impedances, measure second positions of the probe fixed at a second point, different from the first point, in the body of a patient over at least a further portion of a further respiration cycle of the patient;

measure second impedances between the electrodes affixed to the body of the patient while measuring the second positions, formulate respective second indicators of a respiration state of the patient at the second positions, the respective second indicators being formulated in response to the second impedances;

generate a functional relationship between changes of the first and second positions and changes of the first and second indicators respectively, extract parameters from the functional relationship, and wherein, after the probe is moved to a third point of the body, the processor is configured to:

measure third positions of the probe at the third point during a subsequent respiration cycle of the patient; and apply the parameters to the third positions so as to compensate for respiratory motion, wherein extract the parameters comprises computing a centroid of the measured first and second positions.

9. The apparatus according to claim 8, and comprising determining respective vectors from the first positions to the centroid.

10. The apparatus according to claim 9, wherein the functional relationship comprises a relationship defining the respective vectors in terms of the respective indicators.

11. The apparatus according to claim 9, wherein compensating for the respiratory motion at the second point comprises determining coordinates of the second point in response to the respective indicators and the respective vectors.

12. The apparatus according to claim 8, wherein the processor is configured to measure further impedances between the probe and the electrodes, and formulate at least one of the first positions and the second positions in response to the further impedances.

13. The apparatus according to claim 8, and comprising electrodes affixed to the body of the patient, wherein the processor is configured to measure impedances between the electrodes and the probe, and formulate at least one of the first positions and the second positions in response to the impedances.

* * * * *